United States Patent
Ostertag et al.

(10) Patent No.: US 11,813,146 B2
(45) Date of Patent: *Nov. 14, 2023

(54) INCONTINENCE DIAPER

(71) Applicant: PAUL HARTMANN AG, Heidenheim (DE)

(72) Inventors: Wolfgang Ostertag, Gerstetten (DE); Anselm Ebert, Hoechberg (DE); Ruediger Kesselmeier, Burlafingen (DE); Albena Drumeva-Eberisu, Langenau (DE)

(73) Assignee: PAUL HARTMAN AG, Heidenheim (DE)

( * ) Notice: Subject to any disclaimer, the term of this patent is extended or adjusted under 35 U.S.C. 154(b) by 256 days.

This patent is subject to a terminal disclaimer.

(21) Appl. No.: 17/182,395

(22) Filed: Feb. 23, 2021

(65) Prior Publication Data

US 2021/0220187 A1    Jul. 22, 2021

Related U.S. Application Data

(63) Continuation of application No. 16/066,888, filed as application No. PCT/EP2016/082005 on Dec. 20, 2016, now Pat. No. 10,993,850.

(30) Foreign Application Priority Data

Dec. 29, 2015   (DE) ..................... 10 2015 226 814.4

(51) Int. Cl.
*A61F 13/15* (2006.01)
*A61F 13/49* (2006.01)
(Continued)

(52) U.S. Cl.
CPC .. *A61F 13/49019* (2013.01); *A61F 13/49001* (2013.01); *A61F 13/49015* (2013.01);
(Continued)

(58) Field of Classification Search
CPC ................ A61F 13/49019; A61F 13/49; A61F 13/49015; A61F 13/55115; A61F 13/5633;
(Continued)

(56) References Cited

U.S. PATENT DOCUMENTS 6,579,275 B1   6/2003   Pozniak et al.
8,480,830 B2   7/2013   Chang et al.
(Continued)

FOREIGN PATENT DOCUMENTS

CN   102088943 A   6/2011
CN   102448417 A   5/2012
(Continued)

OTHER PUBLICATIONS

European Office Action dated Sep. 9, 2019.
(Continued)

*Primary Examiner* — Jacqueline F Stephens
(74) *Attorney, Agent, or Firm* — John Rizvi; John Rizvi, P.A.—The Patent Professor@

(57) ABSTRACT

There is provided herein an incontinence diaper (2) which has rear lateral sections (22) of the incontinence diaper (2) which can be brought into overlapping arrangement with a front region (12) exterior, to which the lateral sections can then be removably adhered via respective closure means (28). The rear lateral sections (22) have an elastic region (42), and the extension (Q) of the rear lateral sections (22) comprises a proximal half (38) which adjoins the rear longitudinal edge (18) and a freely ending distal half (40) in the transverse direction (10), and wherein, the respective elastic region (42) is arranged completely within the proximal half (38) and has a distance of maximally 30 mm from the rear longitudinal edge (18) in the transverse direction
(Continued)

(10), and each rear lateral section (22) is substantially non-stretchable in the entire distal half (40).

15 Claims, 7 Drawing Sheets

(51) Int. Cl.
  *A61F 13/551* (2006.01)
  *A61F 13/56* (2006.01)
(52) U.S. Cl.
  CPC .... *A61F 13/55115* (2013.01); *A61F 13/5633* (2013.01); *A61F 13/5644* (2013.01); *A61F 2013/49077* (2013.01)
(58) Field of Classification Search
  CPC ............ A61F 13/5644; A61F 13/49077; A61F 13/49006; A61F 13/49058
  See application file for complete search history.

(56) References Cited

U.S. PATENT DOCUMENTS

| | | | |
|---|---|---|---|
| 8,529,536 B2 | 9/2013 | Tsang et al. | |
| 10,993,850 B2* | 5/2021 | Ostertag | ........... A61F 13/49001 |
| 2003/0109844 A1 | 6/2003 | Gibbs | |
| 2006/0241560 A1 | 10/2006 | Chang et al. | |
| 2007/0066950 A1 | 3/2007 | Nelson | |
| 2007/0234529 A1* | 10/2007 | Middlesworth | ....... A61F 13/622 |
| | | | 604/389 |
| 2007/0246152 A1 | 10/2007 | Chang et al. | |
| 2009/0306617 A1 | 12/2009 | Tsang et al. | |
| 2011/0245794 A1 | 10/2011 | Hermansson | |
| 2012/0065607 A1 | 3/2012 | Konig et al. | |
| 2016/0100994 A1 | 4/2016 | Roe et al. | |

FOREIGN PATENT DOCUMENTS

| | | | |
|---|---|---|---|
| CN | 104958140 A | 10/2015 | |
| CN | 104970922 A | 10/2015 | |
| DE | 102009022529 A1 | 12/2010 | |
| DE | 10196559 T1 | 11/2013 | |
| EP | 0650714 A1 | 5/1995 | |
| EP | 2029079 B1 | 8/2012 | |
| WO | WO-2004021949 A1 * | 3/2004 | ......... A61F 13/5622 |
| WO | 2007035903 A1 | 3/2007 | |
| WO | 2007070023 A1 | 6/2007 | |
| WO | 2007149017 A1 | 12/2007 | |
| WO | 2009145860 A2 | 12/2009 | |
| WO | 2009157835 A1 | 12/2009 | |
| WO | 2011106648 A1 | 9/2011 | |

OTHER PUBLICATIONS

International Search Report and Written Opinion from PCT/EP2016/082005 dated Mar. 29, 2017.
German Search Report.
Chinese Office Action dated Jun. 30, 2020.

* cited by examiner

INCONTINENCE DIAPER

This application claims priority as a continuation application from U.S. patent application Ser. No. 16/066,888 filed Jun. 28, 2018; which claims priority to International Application No. PCT/EP2016/082005 filed Dec. 20, 2016, which claims priority to DE 10 2015 226 814.4 filed Dec. 29, 2015 the entire contents of all of which are incorporated herein by reference in their entireties.

The invention relates to a disposable incontinence diaper, having a main part having an absorbent element and a longitudinal direction and a transverse direction, comprising a front region having forward lateral longitudinal peripheries, a back region having rearward lateral longitudinal peripheries, and disposed therebetween a crotch region that comes to lie between the legs of a user, and rearward side portions which are joined to both sides of the back region and which in the transverse direction of the disposable incontinence diaper extend beyond the rearward lateral longitudinal peripheries of the main part and in the region of that end of said rearward side portions that is free in the transverse direction have in each case at least one closure means, whereas no side portions are joined to the front region but the forward lateral longitudinal peripheries of the main part form a free-ending longitudinal periphery of the diaper, wherein the rearward side portions for placing and closing the disposable incontinence diaper on a user are in each case capable of being placed around the body of the user in a circumferential direction and of being moved to an arrangement that overlaps with an external side of the front region, said rearward side portions then being capable of being in each case releasably adhered to said external side of the front region by way of the respective closure means, wherein the rearward side portions in a planar spread-out but not elongated state have an extent (Q) in the transverse direction beyond the respective rearward lateral longitudinal periphery and within this extent (Q) are elastically elongaable in the transverse direction and to this end have an elastic or elasticized region that extends in the transverse direction and in the longitudinal direction, wherein this extent (Q) in the transverse direction of the rearward side portions comprises a proximal half that adjoins the rearward lateral longitudinal periphery and a free-ending distal half.

A disposable incontinence diaper of this type is a so-called T-shaped diaper which fundamentally differs from other diaper concepts. In the case of T-shaped diapers of this type as are described, for example, in WO 2007/035903 A1, side portions are joined to the main part only in the back region, while the diaper in the front region does not have any additional side portions joined thereto but is delimited by respective lateral longitudinal peripheries of the main part. The rearward side portions in most instances project in the longitudinal direction of the diaper, but are typically shorter than the extent of the rear lateral longitudinal peripheries of the main part in the back region. The rearward side portions of T-shaped diapers in the transverse direction extend in such a manner that said rearward side portions can be brought to overlap the external side of the front region of the main part, in order that closure means that are provided in the region of the respective free ends of the rearward side portions can be closed on the external side of the main part of the diaper.

As opposed thereto, so-called belt diapers in which very long belt portions extend away on both sides in the transverse direction from the back region of the main diaper part are widely known, said belt portions being dimensioned in such a manner that the latter can be closed on themselves around the entire stomach circumference of the user. When a belt diaper is being placed for wearing, the product is placed from behind against the hip or back region of the user, and the two belt portions are thereafter closed directly on one another on the stomach side of the user. No oblique tensile forces whatsoever are introduced into the belt or the main part herein, but a force that acts only in the circumferential direction of the hip is exerted on both belt portions. Thereafter, the main diaper part is retrieved from between the legs of the user and by means of further closure elements is positioned and fixed in most instances against the external side of the previously closed belt. Regions of the belt portions have also already been configured so as to be elastic, e.g. EP 2 029 079 B1.

In the case of the T-shaped diapers being discussed here, in which the rearward side portions are closed on the external side of the front region of the main diaper part, high tensile forces are often introduced into the side portions and into the main diaper part when closing, because the user or a carer when placing the diaper endeavors to establish an obvious overlap situation between the rearward side portions and the front region of the main part and herein to simultaneously introduce the tensile force that is required for a tight fit of the diaper into the overall system such that the diaper is also durably held on the user. Oblique tensile forces also arise herein in the care situation, the former thus being tensile forces which besides a component in the transverse direction have a component in the longitudinal direction, this leading to critical situations in the region where the rearward side portions join the main part. Tearing of the side portions or severing of the join connection often arises therein. In the case of belt diapers as well as in the case of diapers having side portions joined to the front and the rear this problem arises to a significantly lesser extent. The kinematics of placing for wearing in the case of belt diapers is completely different, and in the case of diapers having rearward and forward side portions a typical placing situation is already established by way of the overlap between the respective rearward and forward side portions.

The present invention is based on the object of improving a T-shaped disposable incontinence diaper of the type mentioned at the outset to the extent that tensile forces, in particular oblique tensile forces, that occur when the diaper is being placed on the body of the user lead to a lesser extent to damage to the diaper materials, wherein a cost-effective production capability of the article is nevertheless to be implemented.

This object in the case of a disposable incontinence diaper of the type mentioned is achieved according to the invention in that the respective elastic or elasticized region of the rearward side portions is disposed completely within the proximal half and reaches up to the assigned rearward lateral longitudinal periphery, or has a spacing in the transverse direction from the rearward lateral longitudinal periphery of at most 30 mm, and in that the respective rearward side portions in the entire distal half are configured so as to be substantially non-elongatable.

By way of the present invention it has been recognized that elastically elongatable regions at the rearward side portions do not contribute toward any improvement when said elastically elongatable regions in the transverse direction are disposed so as to be too remote from the back region of the main part of the diaper. On the contrary, said elastically elongatable regions lead to the user, or a carer, feeling obliged to apply an even greater tensile force and elongation. It has been established that elongatable, in particular elastically elongatable, regions in the respective distal portion of the rearward side portions can be dispensed with without any replacement, this reducing the production costs as a result of the reduction in terms of elastic or elasticized materials which in most instances are expensive.

When mention of the properties "elastically elongatable", "elongatable", or "non-elongatable" is made in the present application, the respective property is at all times intended to refer to the transverse direction of the disposable incontinence diaper. With a view to quantifiably delineating elastically elongatable regions from non-elongatable or not elastically elongatable regions, reference is made to the measuring or testing methods described further below.

It furthermore proves advantageous for the respective elastic or elasticized region of the rearward side portions to reach up to the assigned rearward lateral longitudinal periphery, without however overlapping the rearward lateral longitudinal periphery. In a refinement of this inventive concept, the spacing in the transverse direction of a respective elastic or elasticized region of the rearward side portions from the rearward lateral longitudinal periphery is at most 20 mm, in particular at most 10 mm. This opens up the possibility of there being no elongatable side portion materials provided in the direct transition from that region of the side portion that lies outside the main part to a region of the side portion that overlaps the main part, this increasing the stability of the join connection.

It therefore also proves advantageous for the two rearward side portions to be non-releasably joined to the main part conjointly with a non-elongatable region that overlaps the main part.

It is furthermore proposed that the side portions are configured such that in the introduction of conventional forces that simulate the use situation in the transverse direction, the respective elastic or elasticized region in the transverse direction is elongatable by at least 70%, in particular by at least 80%, further particularly by at least 90%. This herein refers to an elongation capability which is not associated with any durable significant plastic deformation, let alone any damage to the material, but one that permits and causes an elastic recovery of the elongated side portions. The values are determined by the corresponding application of the measuring or testing methods described further below.

In the simplest and preferred case, the rearward side portions are configured so as to be rectangular, that is to say that said side portions are delimited by peripheries that run in the transverse direction and in the longitudinal direction of the disposable incontinence diaper. At least the proximal half of the extent (Q) of the side portions is preferably delimited by the peripheries running in the transverse direction.

A respective elastic or elasticized region is also advantageously configured so as to be rectangular, that is to say that said regions are delimited by peripheries that run in the transverse direction and in the longitudinal direction of the disposable incontinence diaper. Furthermore preferably, a respective elastic or elasticized region extends across the full length of the side portions (in the longitudinal direction of the disposable incontinence diaper).

The extent of a respective elastic or elasticized region in the transverse direction in the non-elongated state is preferably 40 to 120 mm, in particular 60 to 100 mm.

The extent (Q) of the planar spread-out but not elongated rearward side portions beyond the rearward lateral longitudinal periphery of the main part in the transverse direction of the disposable incontinence diaper is preferably 130 to 280 mm, in particular 170 to 250 mm.

The extent (B) of the rearward side portions in the longitudinal direction in the region of the joint with the main part is 100 to 200 mm, in particular 120 to 170 mm.

An extent (QE) of a respective elastic or elasticized region in the transverse direction, and a maximum extent (Q) of the rearward side portions beyond the respective rearward lateral longitudinal periphery, are preferably dimensioned in such a manner that the mutual ratio of the extents (QE/Q) is 0.20<QE/Q<0.50, in particular 0.30<QE/Q<0.45.

In the case of the T-shaped disposable incontinence diaper according to the invention it has proven particularly advantageous for the extent (Q) in the transverse direction of the rearward side portions beyond the respective rearward lateral longitudinal periphery, and a maximum extent (B) in the longitudinal direction of the rearward side portions, to be dimensioned such that the mutual ratio of the extents (Q/B) is 1.0<Q/B<2.0. In the case of belt diapers, this ratio is higher by a multiple.

It is furthermore proposed that the two rearward side portions in the longitudinal direction have a spacing from a rearward transverse periphery of the main part of at least 1 mm, in particular of at least 5 mm, in particular of at least 10 mm, in particular of at least 15 mm, in particular of at most 50 mm. It is guaranteed on account thereof that the transverse tensile forces that when placing are exerted by way of the closure means and herein are introduced into the back region of the main part are "distributed" to a comparatively large portion of the main part.

It furthermore proves advantageous for a straight line that extends in the transverse direction and is tangent to the respective closure means on the crotch-facing side to intersect the absorbent element. This can preferably be implemented when the two rearward side portions in the longitudinal direction have a spacing from the rearward transverse periphery of the main part, as has been mentioned above. It is provided in particular that a straight line that extends in the transverse direction, and in the longitudinal direction bisects the side portions in the region of the joint with the main part, intersects the absorbent element. This stabilizes the bearing of the absorbent element and supports a correct fit of the diaper.

It furthermore proves advantageous for each rearward side portion to have exactly one closure means. The closure means are typically a tab from a single-layer or multiple-layer flat material which, proceeding from a configuration that is typically folded inward onto the side portion about a distal longitudinal periphery of the viewed side portion, is capable of being unfolded to an operating position that is folded outward. A respective closure means is equipped with adhesive and/or mechanically adhering regions, layers, or elements, such as hook-and-loop materials, for example, in a manner known per se which therefore does not require any further description. In as far as the side portion has exactly one closure means, it proves advantageous for said closure means to be provided in a distal region of the side portion so as to be approximately centric in the longitudinal direction. It furthermore proves advantageous for the respective closure means to have an extent in the longitudinal direction that is between 25% and 75% of the extent B of the side portion in the longitudinal direction. Furthermore, the respective closure means in the folded-in and the unfolded state are preferably configured so as to be rectangular. Said closure means in the non-active configuration ex works are preferably folded inward onto themselves.

In terms of the dimensions of the main part of the disposable incontinence diaper it has proven advantageous for the extent of the main part in the transverse direction in the back region and/or in the front region to be 250 mm to 550 mm, in particular 300 to 520. The front region and the back regions of the main part preferably have the same transverse extent (measured in mm).

The extent of the main part in the longitudinal direction is preferably 700 to 1200 mm, in particular 800 to 1100 mm. The main part can be provided with a constriction in the transverse direction, consequently a leg opening contour, in the crotch region. In an alternative embodiment, the main part is configured so as to be rectangular.

The elastic or elasticized regions can be implemented by way of means that per se are commonplace to a person skilled in the art. For example, portions per se of elastic materials such as elastic films or elastic non-wovens, can thus be joined to non-elongatable portions of the side portions by joining methods such as adhesive bonding or thermal welding or ultrasonic welding.

A further possibility for achieving an elastification in regions lies in that the side portions in regions are preferably "activated" by a technology that has become known as "ring rolling". This technology is described, for example, in EP 0 650 714 A1. A material that per se is not elongatable, for example a non-woven/film laminate, is super-elongated by "ring rolling" by way of an excessive deflection between mutually meshing rollers. In this super-elongated state, that material of the laminate that previously was not elongatable per se does not offer any substantial resistance to being stretched in terms of length. By way of a combination with an elastically elongatable element within a laminate of this type, an elastic elongation capability can be achieved in the correspondingly treated region. As an alternative thereto, elasticizing means such as elastic film portions or threads, in particular Lycra or Spandex threads in the pre-tensioned state, can be connected in regions with the flat materials, in particular non-woven materials, that form the remainder of the side portions (stretch-bonding).

The rearward side portions in the use situation are brought to overlap the external side of the front region of the main part, in order that closure means that are provided in the region of the respective free ends of both rearward side portions can be closed on the external side of the main part of the diaper. To this end, the closure means and at least one region of the external side of the main part are configured as a closure system. To this end, the closure means have in particular mechanical closure elements such as hook elements, in particular also in combination with adhesively bonding regions, by means of which the closure means are capable of being rendered so as to engage in a releasable adhering manner with the external side of the main part. To this end, it has proven advantageous for the external side of the main part to be at least in regions, preferably completely, formed by a correspondingly configured non-woven. Alternatively, it is possible for a separate hook pile element to be provided on the external side in the front region of the main part, said separate hook pile element serving as a landing zone for the closure means of the side portions.

Although the rearward side portions are considerably shorter in the transverse direction than in the case of belt diapers, it proves advantageous for the rearward side portions ex works to be folded onto themselves about at least two side portion folding axes that run in the longitudinal direction and for the folded configuration obtained in this way to be preferably fixed ex works, for instance by way of individual joints, in particular adhesively bonded or ultrasonically welded spots, which for unfolding the side portions by the user are nevertheless comparatively easy to release by hand. In this case, a single closure means that in the longitudinal direction is positioned so as to be approximately centric on the side portions preferably proves to be advantageous, wherein the joints do not acquire the folded-in closure means but are disposed so as to be outside the closure means in the longitudinal direction. When the part-regions that bear on one another are releasably fixed by the aforementioned measures about the at least one closure means that is tucked inward, or in the longitudinal direction above or below the tucked-in closure means, the tucked-in closure means thus forms a holding region that is readily capable of being gripped for unfolding the respective side portion.

It furthermore proves advantageous for the rearward side portions ex works to be folded onto themselves about at least two side portion folding axes that run in the longitudinal direction, part-regions of the rearward side portions that are folded onto one another being defined and delimited by said side portion folding axes, and in that a part-region that is outboard in the transverse region is configured so as to be substantially non-elongatable. On account thereof, in particular the gripping capability and the unfolding capability of the side portion as well as of the folded-in closure means are improved.

It furthermore proves advantageous for a part-region that inwardly adjoins the outboard part-region, proceeding from the outer folding axis that runs in the longitudinal direction, by way of at least 50% of the area of said part-region to be configured so as to be non-elongatable. These at least 50% of the area are thus determined proceeding from the outboard folding axis in that, an imaginary line that is parallel with the folding axis, proceeding from the latter, is moved inward in a quasi scanning manner in the transverse direction until said imaginary line meets an elongatable region. The scanned area is then determined and compared to the overall plan view area of the part-region. It is achieved on account thereof that the part-region that in the transverse region is outboard, and the part-region inwardly adjoining the latter, in a planar manner bear on one another across a very large non-elongatable area (of at least 50% of the area of the last-mentioned part-region) which consequently is free of elastic or elasticizing elements.

The extent (U) of a respective non-elongatable region of the part-region that inwardly adjoins the outboard part-region, proceeding from the outer folding axis that runs in the longitudinal direction, in the transverse direction up to the start of an elongatable region is preferably at least 15 mm, in particular at least 20 mm, furthermore in particular at least 25 mm, further preferably at least 30 mm, but preferably at most 100 mm, furthermore preferably at most 70 mm.

It is furthermore proposed that a respective side portion folding axis that in the unfolded state is inboard, thus adjacent to the rearward lateral longitudinal periphery of the main part, runs within the elastic or elasticized region of the respective side portion. On account thereof, the stiffening effect of each fold which is undesirable per se in the case of a flat material can be reduced.

However, it proves advantageous for a respective side portion folding axis that in the unfolded state is further outboard in the transverse direction to run within the non-elongatable region of the rearward side portions. The stiffening effect of the folding axis can indeed be desirable specifically therein, since on account thereof the introduction of the tensile force by way of the closure means is distributed more uniformly to the side portions.

It is furthermore proposed that the rearward side portions ex works are folded onto themselves about exactly two side portion folding axes that run in the longitudinal direction such that exactly three part-regions of the side portions are formed, and such that the central part-region, proceeding from the outer folding axis that runs in the longitudinal direction, by way of at least 50% of the area thereof is configured so as to be non-elongatable.

It preferably applies to the folded-in configuration of the rearward side portions that an extent (A) in the transverse direction of the rearward side portions that are folded onto themselves beyond the respective rearward lateral longitudinal periphery, and an extent (B) in the longitudinal direction of the rearward side portions that are folded onto themselves, are dimensioned such that the mutual ratio of the extents (A/B) is 0.5<A/B<1.

Prior to the ex works packaging of the disposable incontinence diapers, the main part, together with the rearward side portions that are folded onto themselves, is preferably ex works folded inward onto itself about a first and a second main part folding axis that in each case run in the longitudinal direction in such a manner that the rearward side portions on both sides come to lie so as to at least partially overlap one another in the direction of thickness, thus in a manner orthogonal to a plane that encloses the longitudinal direction and the transverse direction. Prior to the ex works packaging of the disposable incontinence diapers, the main part together with the rearward side portions that are folded onto themselves, and preferably subsequent to the folding about main part folding axes that run in the longitudinal direction as described above, is furthermore preferably additionally it works folded inward onto itself about one or two main part folding axes that run in the transverse direction.

Further features, details and advantages of the invention are provided by the accompanying patent claims and by the graphic representation and description that follows of a preferred embodiment of the disposable incontinence diaper according to the invention. In the drawing:

Figure 1:
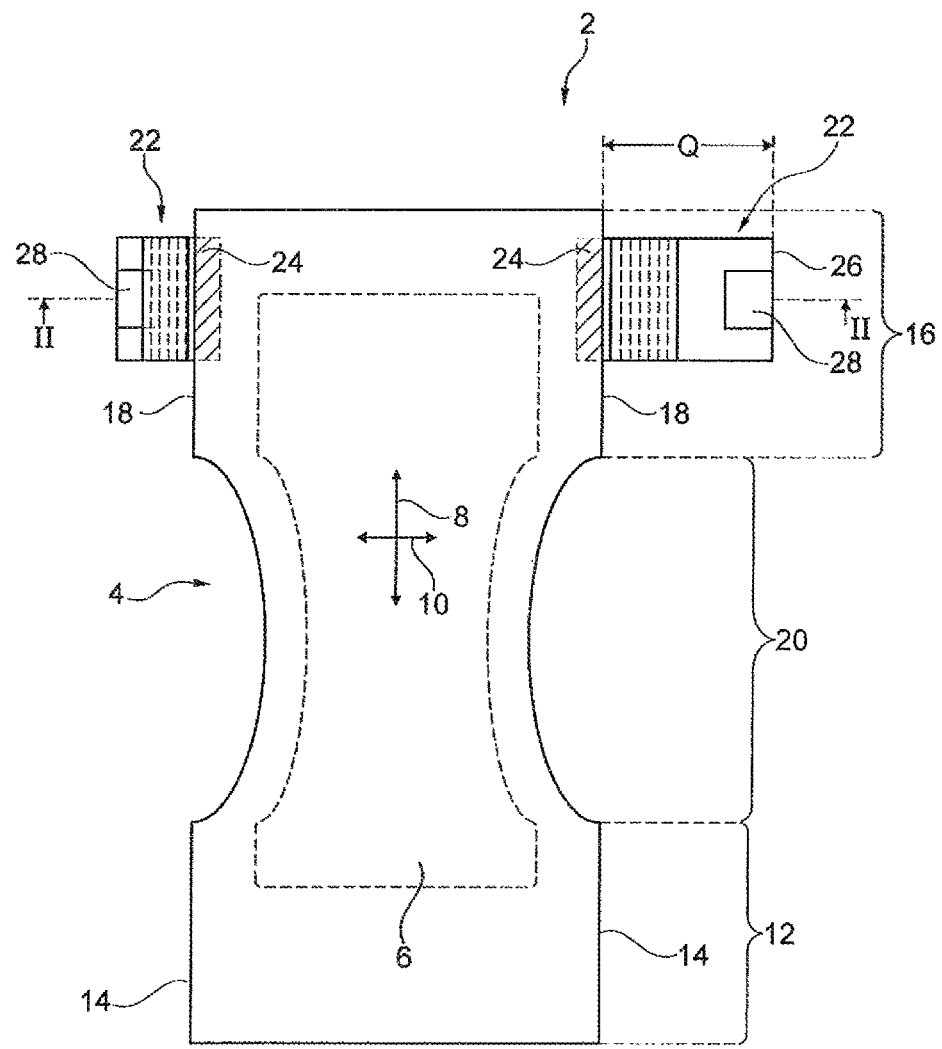
FIG. 1 shows a plan view of a disposable incontinence diaper according to the invention, in a planar spread-out but not elongated state.
Figure 4A:
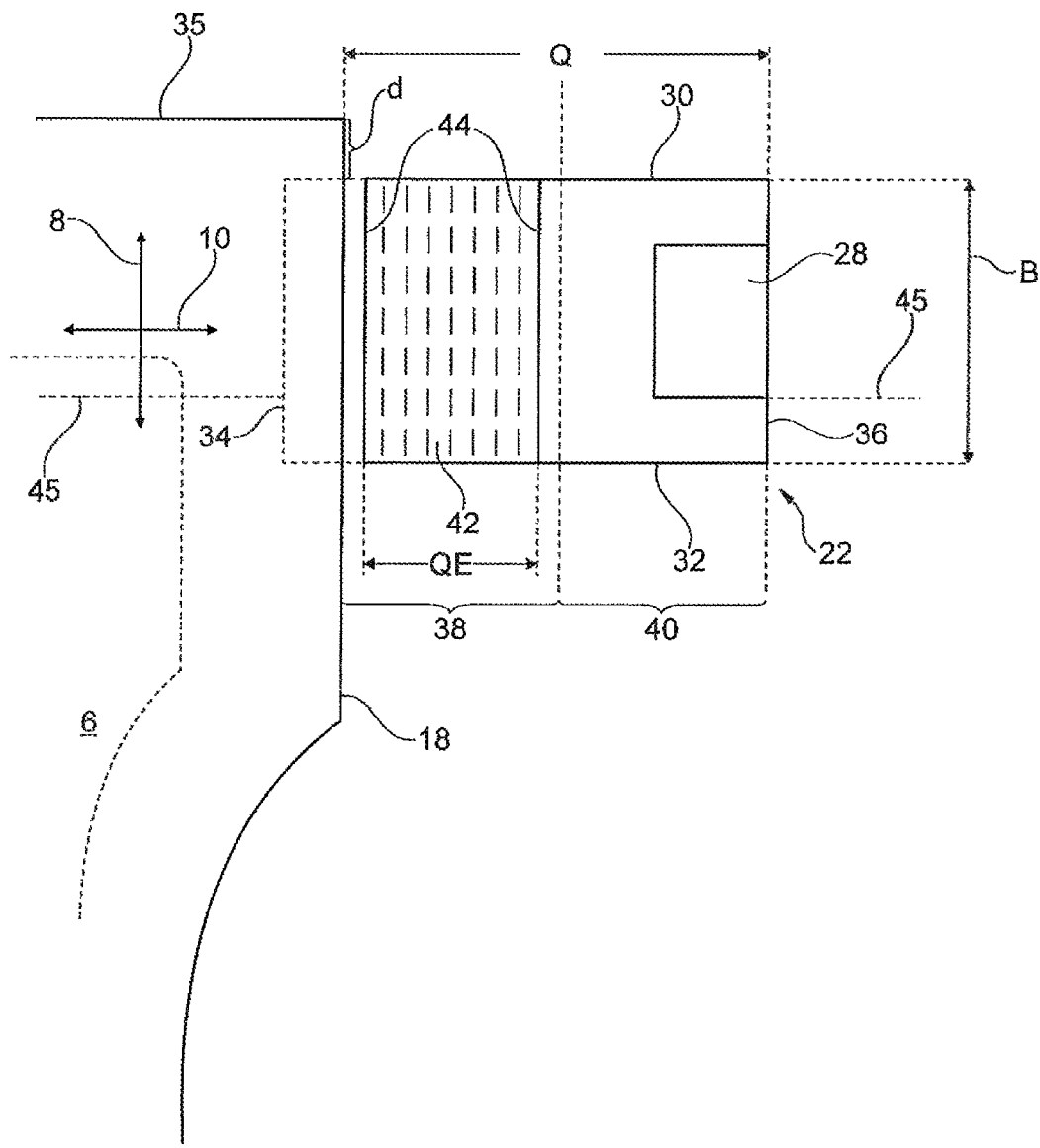
Figure 5:
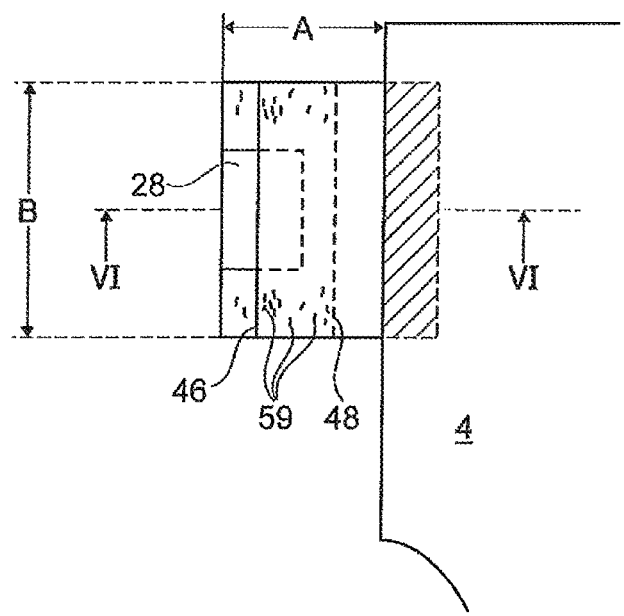
Figure 6:
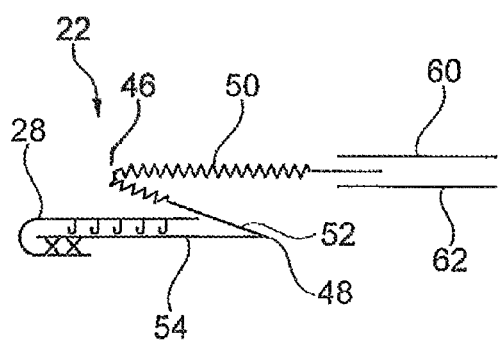
Figure 7:
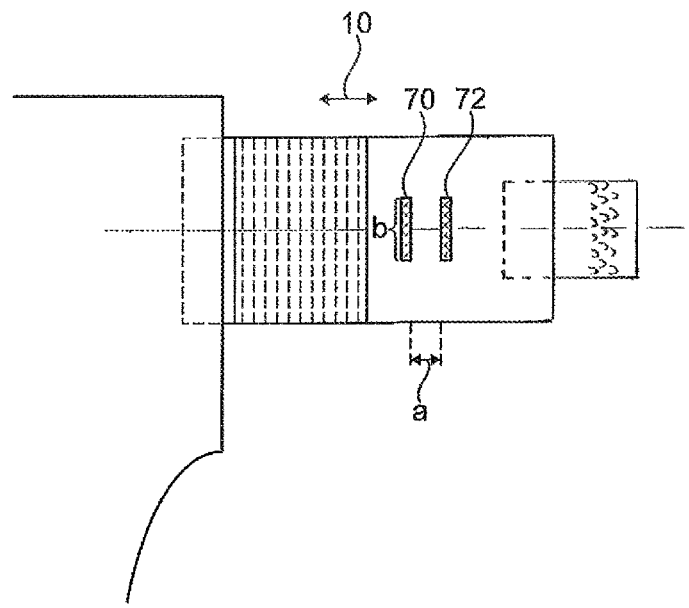
Figure 8:
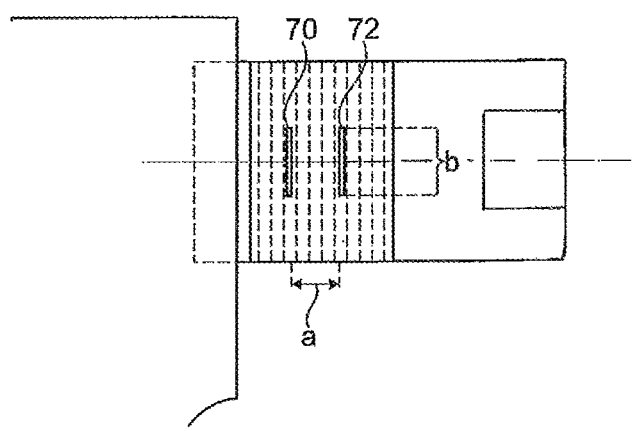

FIGS. 4a, b, c show in each case an enlarged and partial illustration of the diaper as per FIG. 1 in the region of a rearward side portion, in a planer spread-out but not elongated state, having dimensions and folding axes, respectively;

FIG. 5 shows an enlarged illustration of the diaper as per FIG. 1 in the region of a rearward side portion, in a configuration in which said diaper is folded onto itself;

FIG. 6 shows a sectional view by way of the section plane VI-VI of FIG. 5;

FIGS. 7 and 8 show an illustration of the diaper according to FIG. 4, having clamps of a device for determining the elongation capability.

Figure 3:
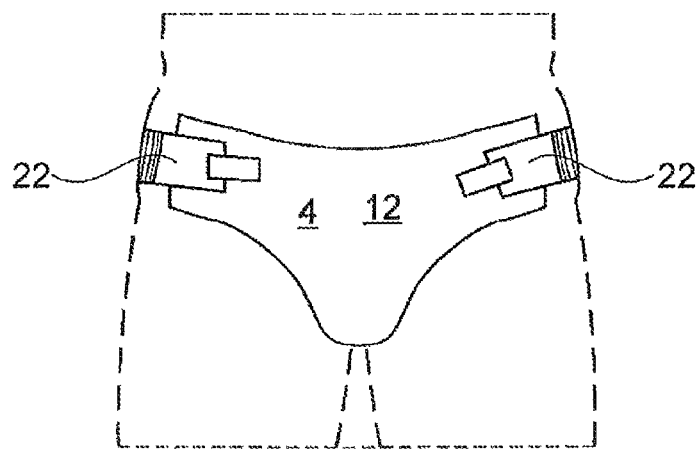
FIG. 3 shows a schematic illustration of the diaper in the worn state.

The figures show a disposable incontinence diaper according to the invention, which in its entirety is identified by the reference sign 2, in the so-called T-shape. The diaper 2 comprises a main part that in its entirety is identified by the reference sign 4, having an absorbent element 6 that absorbs bodily fluids. The absorbent element 6 preferably comprises cellulose fibers and super-absorbent polymer particles (SAP). In the case of the diaper 2, a longitudinal direction 8 and a transverse direction 10 are distinguishable, wherein the latter in the worn state of the diaper corresponds to the circumferential direction of the hip of the user. The main part 4 comprises a front region 12 having forward lateral longitudinal peripheries 14, a back region 16 having rearward lateral longitudinal peripheries 18, and disposed therebetween a crotch region 20. In the case of the T-shaped diaper 2, rearward side portions 22 which in the transverse direction 10 extend laterally beyond the rearward lateral longitudinal peripheries 18 are provided only in the back region 16 of the main part 4, said rearward side portions 22 in the region of the rearward lateral longitudinal peripheries 18 being non-releasably joined to the back region 16 of the main part 4 in an overlap region 24. The rearward side portions 22 in the region of the free end 26 thereof in the transverse direction 10 have in each case at least one closure means 28. The closure means 28 is configured in the form of a preferably rectangular tab and is folded in onto itself. The closure means can be opened, that is to say unfolded again, in the use situation, so as to place the disposable incontinence diaper 2 on a user, wherein the side portions 22 are brought to overlap the front region 12 of the main part 4 and the closure means are fastened so as to releasably adhere to the external side of the front part of the main part (schematically illustrated in FIG. 3).

As can best be seen from FIG. 4a, the side portions 22 are preferably configured so as to be rectangular, wherein the latter are delimited by peripheries 30, 32 that run in the transverse direction 10 and by peripheries 34, 36 that run in the longitudinal direction 8. The rearward side portions 22 in the planar unfolded or spread-out but not elongated state illustrated in FIG. 42 have an extent Q of 200 mm beyond the rearward lateral longitudinal periphery 18 in the transverse direction 10. This extent Q of the side portions 22 outside the main part 4 in the transverse direction 10 comprises a proximal half 38 that adjoins the rearward lateral longitudinal periphery 18, and a free-ending distal half 40 of the side portions 22. The side portions 22 in the longitudinal direction 8 have a spacing d from a rearward transverse periphery 35 of the diaper of preferably 5 to 50 mm. The extent (B) of the side portions in the longitudinal direction in the case illustrated is 140 mm.

The side portions 22 outside the main part 4 are configured so as to be elastically elongatable in the transverse direction 10. To this end, said side portions 22 have an elastic or elasticized region 42. This elastic or elasticized region 42 of the rearward side portions 22 is disposed completely within the proximal half 38 of the rearward side portions 22. Said region 42 in the exemplary case illustrated in the transverse direction 10 has a slight spacing of a few millimeters from the rearward lateral longitudinal periphery 18. The elastic or elasticized region 42 is configured so as to be rectangular, and the extent (QE) thereof in the transverse region is delimited by peripheries 44 that extend in the longitudinal direction 8, wherein the peripheries 44 extend across the entire longitudinal extent of the rearward side portions 22.

The rearward side portions in the distal half 40 of the extent Q of the rearward side portions 22 are configured so as to be non-elongatable in the transverse direction 10.

The respective elastic or elasticized region 42 of the rearward side portions 22 can typically be achieved by interposing an elastically elongatable or an elasticized material in the side portions 22. The side portions 22 in this instance are configured by material portions of dissimilar elongation capabilities that are disposed sequentially and joined to one another in the transverse direction 10. Alternatively thereto, elasticizing means in the pre-tensioned state can be connected to flat materials of the rearward side portions 22. Furthermore alternatively, it is possible for flat material laminates that are non-elongatable per se such as, for example, laminates comprising non-elongatable non-wovens and elastic films of the rearward side portions 22 that are joined to said non-wovens in a planar manner, by way of measures known in the prior art, such as by way of so-called "ring rolling", to be "activated", that is to say rendered elastically elongatable, in regions.

The rearward side portions 22 are furthermore disposed on the back region 16 of the main part 4 in such a manner that a straight line 45 that extends in the transverse direction 10 and is tangent to the respective closure means 28 on the crotch-facing side intersects the absorbent element 6.

Figure 2:
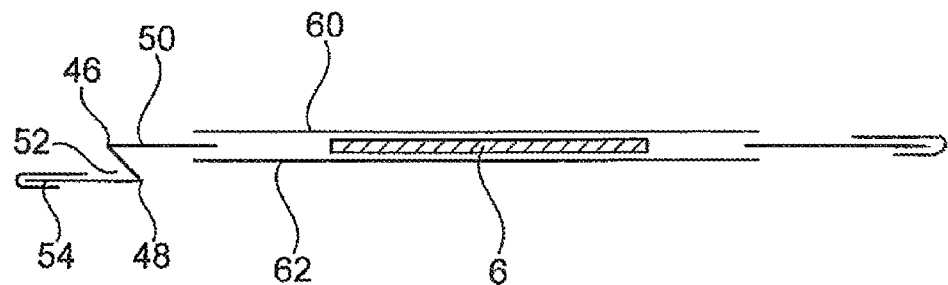
FIG. 2 shows a side view of the diaper as per figure one, by way of the section plane II-II.
Figure 4B:
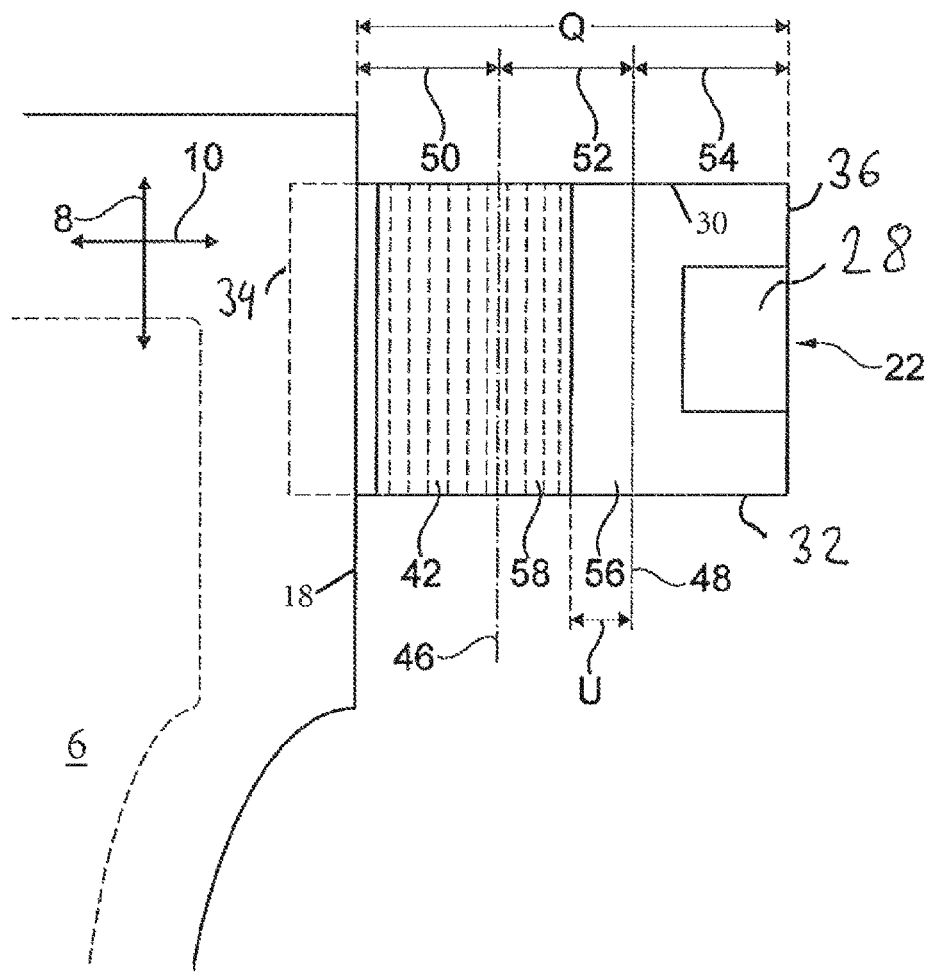
Figure 4C:
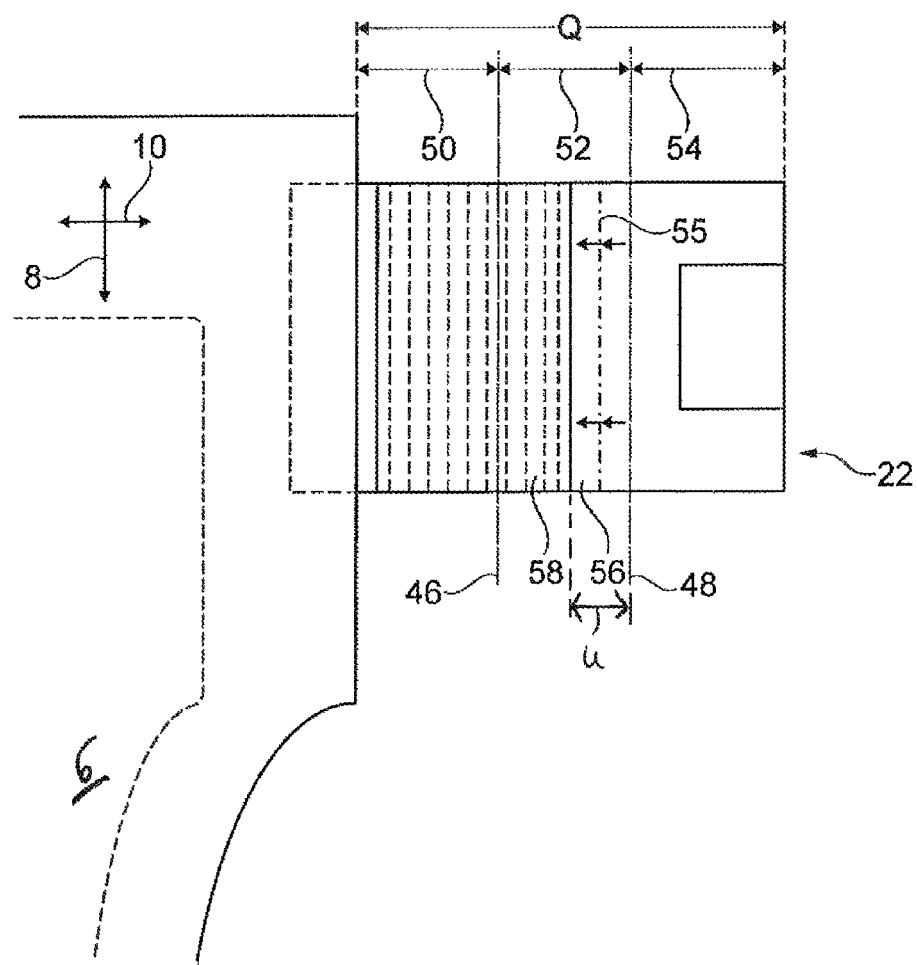

As is illustrated in FIGS. 1, 2 (in each case on the left) and FIGS. 4b, 5, and 6, the rearward side portions 22 ex works are folded onto themselves about at least two side portion folding axes 46, 48 that run in the longitudinal direction 8. The side portion folding axes 46, 48 herein define and delimit part-regions 50, 52, 54 of the rearward side portions 22 that are folded onto one another (FIG. 4b). It can be seen that the side portion folding axis 46 that is adjacent to the rearward lateral longitudinal periphery 18, thus the inboard side portion folding axis 46, runs within the elastic or elasticized region 42, while the side portion folding axis 48 that in the transverse direction 10 is further outboard runs outside the elastic or elasticized region 42, thus within a non-elongatable region of the side portions 22. The part-region 52 which inwardly adjoins that part-region 54 that in the transverse direction 10 is outboard, proceeding from the outer folding axis 48 that runs in the longitudinal direction 8, by way of at least 50% of the area of said part-region 52 is configured so as to be non-elongatable. In order for this non-elongatable area to be determined, an imaginary line 55 that is parallel with the folding axis 48, proceeding from the latter, is moved inward in a quasi scanning manner in the transverse direction 10 in the direction of the main part 4 (this being visualized by arrows in FIG. 4c) until said imaginary line 55 meets an elongatable region 58. The area thus scanned is at least 50% of the entire area in the plan view of the part-region 52 in the non-elongated state. The part-region 52 here in the transverse direction 10 has a rectangular outer non-elongatable region 56 of a transverse extent U, and in the transverse direction 10 has a rectangular inner elastically elongatable region 58, said regions 56, 58 being delineated from one another by an imaginary line running in the longitudinal direction 8. As has been discussed, the rectangular outer non-elongatable region 56 herein in the non-elongated state comprises at least half of the entire area in the plan view of the part-region 52. It is also conceivable that the part-region 52 that inwardly adjoins the outboard part-region 54 is configured so as to be non-elongatable across the entire extent of said part-region 52.

FIGS. 5 and 6 schematically show the configuration that is folded onto itself of the rearward side portions 22. The part-regions 50, 52, 54 that are folded toward one another are releasably fixed to one another at the joints 59 illustrated in FIG. 5. These joints 59 are configured by way of measures described at the outset. It proves advantageous for non-elongatable regions to a substantial proportion to be releasably joined to one another in the region of the overlap of the part-regions 52, 54. In FIG. 6 the exemplary joining of the closure means 28 to the external side of the side portion 22 that faces away from the body and the folding back onto the body-facing side of the side portion 22 can also be seen in a schematic illustration. Furthermore to be seen is the schematically illustrated exemplary joining of the rearward side portions 22 between two flat materials, for example a liquid-permeable cover layer 60 (top sheet) and a liquid-impermeable back layer 62 (back sheet) of the diaper main part 4.

The dimension A of the folded configuration of the rearward side portions 22 in the transverse direction 10 outside the main part 4, and the dimension B in the longitudinal direction 8 are illustrated in FIG. 5. The ratio A/B is preferably 0.5<A/B<1. The respective ratio Q/B of the side portions 22 in the planar spread-out but not elongated state is preferably 1.0<Q/B<2.0 and is illustrated in FIG. 4a. The ratio of QE, thus the extent of the elastic or elasticized region 42 in the transverse direction, to Q is preferably 0.20<QE/Q<0.50, in particular 0.30<QE/Q<0.45.

In as far as it should not be obvious in the individual case whether a side portion region is elastically elongatable or non-elongatable, the following testing method is specified for the quantitative delineation of the terms non-elongatable, elongatable, or elastically elongatable, respectively:

The elongation capability herein can be determined directly on the side portion 22 of the diaper. To this end, a respective region of a side portion 22 is chucked between two clamping jaws 70, 72 of a defined, identical clamping jaw width b of 50 mm, wherein the clamping jaw spacing a is 30 mm. The clamping jaw width b herein extends in the longitudinal direction 8, and the clamping jaw spacing a extends in the transverse direction 10, wherein the side portion 22 is in the planar spread-out but not elongated state. In as far as the region to be detected should have an extent of less than 30 mm in the transverse direction 10, the clamping jaw spacing a is chosen so as to be correspondingly smaller. The test is performed proceeding from a preliminary force of 0.2 N between the clamping jaws 70, 72. Proceeding therefrom, the clamping jaws 70, 72 are diverged in the transverse direction 10 at a constant speed of 100 mm/min until a force of 15 N is reached, and substantially immediately upon reaching the force of 15 N converged again, specifically again at a constant speed of 100 mm/min until the value of the preliminary force of 0.2 N is reached. The initial clamping jaw spacing L0 in mm when reaching the preliminary force of 0.2 N is noted, on the one hand. Furthermore, the clamping jaw spacing L1 in mm when reaching the force of 15 N is noted (this is preferably performed in each case in an automated manner by way of the evaluation unit of the testing device). Furthermore, the remaining clamping jaw spacing L2 in mm upon reducing the force to the value of the preliminary force of 0.2 N is noted at the end of the test.

In the case of the elongation capability being tested in the region of the distal half 42 of the rearward side portions 22, the clamping jaws 70, 72 are preferably positioned in such a manner that the latter are disposed outside closure means. To this end, the closure means can be folded outward as is illustrated in FIG. 7. Testing the area that is covered by the closure means is not required since the side portions therein by virtue of the closure means are typically non-elongatable anyway.

In the case of the elastic elongation capability being tested within the proximal half 38 of the side portions 22, the clamping jaws 70, 72 are preferably disposed so as to be centric in the longitudinal direction 8 in relation to the longitudinal extent of the side portions 22, as is illustrated in FIG. 8. The above test is then carried out. Subsequently, the clamping jaws 70, 72 are repositioned in the longitudinal direction 8 (repositioned toward the top or the bottom, respectively, in FIG. 8) such that regions of the side portion that are adjacent in the longitudinal direction 8 can be detected and the side portion can thus be tested across the entire extent thereof in the longitudinal direction 8.

For the purpose of evaluation, the term elongation is understood to be the ratio between an increase in the clamping jaw spacing upon reaching 15 N and the clamping jaw spacing in the case of the preliminary force of 0.2 N, thus the elongated clamping jaw spacing L1 in mm at 15 N minus L0 in mm divided by L0 in mm, thus elongation [%]=(L1−L0)/L0.

For the purpose of determining the residual (permanently set) elongation, this is understood to be the ratio of the increase in the clamping jaw spacing upon reducing the force to the value of the preliminary force of 0.2 N in relation to the initial clamping jaw spacing (L2−L0) and the initial clamping jaw spacing L0=, thus remaining elongation [%]=(L2−L0)/L0.

In the context of the present invention, the distal half 40 or an arbitrary region of a respective rearward side portion 22 is considered to be non-elongatable when, carrying out the preceding test, each region of the distal half 40 extending 50 mm in the longitudinal direction 8, and each region of the distal half 40 extending 30 mm in the transverse direction 10, permits an elongation of less than 50% in the case of a brief effect of a force of 15 N.

In the context of the present invention, the proximal half 38, or a region 42 of the proximal half 38, or an arbitrary region of a respective rearward side portion 22 is considered to be elastically elongatable when, carrying out the preceding test, the region detected by the clamping jaws at 15 N permits an elongation of at least 60% and upon reducing the force to the value of the preliminary force of 0.2 N a residual (permanently set) elongation of at most 15% remains, specifically also when carrying out the test with clamping jaws that are repositioned in the longitudinal direction 8. The side portion 22 is thus tested across the entire extent thereof in the longitudinal direction 8.

In the case of the material of a side portion chucked between the clamping jaws breaking prior to the maximum force of 15 N being reached when the preceding test is carried out, the breaking force thus being less than 15 N/50 mm, the material will be considered as unsuitable for carrying out the invention.

The invention claimed is:

1. A disposable incontinence diaper (2), having a main part (4) having an absorbent element (6) and a longitudinal direction (8) and a transverse direction (10), comprising
   a front region (12) having forward lateral longitudinal peripheries (14),
   a back region (16) having rearward lateral longitudinal peripheries (18), and disposed therebetween a crotch region (20) that comes to lie between the legs of a user, and
   rearward side portions (22) which are joined to both sides of the back region (16) and which in the transverse direction (10) of the disposable incontinence diaper (2) extend beyond the lateral rearward longitudinal peripheries (18) of the main part (4) and in the region of that end (26) of said rearward side portions (22) that is free in the transverse direction (10) have in each case at least one closure means (28), whereas no side portions (22) are joined to the front region (14) but the forward lateral longitudinal peripheries (14) of the main part (4) form a free-ending longitudinal periphery of the diaper, wherein
   the rearward side portions (22) for placing and closing the disposable incontinence diaper (2) on a user are in each case capable of being placed around the body of the user in a circumferential direction and of being moved to an arrangement that overlaps with an external side of the front region (12),
   said rearward side portions (22) then being capable of being in each case releasably adhered to said external side of the front region (12) by way of the respective closure means (28),
   the rearward side portions (22) in a planar spread-out but not elongated state have an extent (Q) in the transverse direction (10) beyond the respective rearward lateral longitudinal periphery (18) and within this extent (Q) are elastically elongatable in the transverse direction (10) and to this end have an elastic or elasticized region (42) that extends in the transverse direction (10) and in the longitudinal direction (8),
   this extent (Q) in the transverse direction (10) of the rearward side portions (22) is divided into a proximal half (38) that adjoins the rearward lateral longitudinal periphery (18) and a free-ending distal half (40),
   the respective elastic or elasticized region (42) of the rearward side portions (22) is disposed completely within the proximal half (38) and has a spacing in the transverse direction from the rearward lateral longitudinal periphery (18) of a few millimeters to at most 30 mm, and
   the respective rearward side portions (22) in the entire distal half (40) are configured to be substantially non-elongatable.

2. The disposable incontinence diaper of claim 1, wherein the two rearward side portions (22), conjointly with a non-elongatable region (24) that overlaps the main part (4), are non-releasably joined to the main part (4).

3. The disposable incontinence diaper of claim 1, wherein the respective elastic or elasticized region (42) in the transverse direction (10) is elongatable by at least 70%.

4. The disposable incontinence diaper of claim 1, wherein the extent (Q) in the transverse direction (10) of the rearward side portions (22) beyond the respective rearward lateral longitudinal periphery (18), and a maximum extent (B) in the longitudinal direction (8) of the rearward side portions (22), are dimensioned such that the mutual ratio of the extents (Q/B) is 1.0<Q/B<2.0.

5. The disposable incontinence diaper of claim 1, wherein the two rearward side portions (22) in the longitudinal direction (8) have a spacing (d) from a rearward transverse periphery (35) of the main part (4) of at least 1 mm.

6. The disposable incontinence diaper of claim 5, wherein the two rearward side portions (22) in the longitudinal direction (8) have a spacing (d) from a rearward transverse periphery (35) of the main part (4) of at most 50 mm.

7. The disposable incontinence diaper of claim 1, wherein, a straight line (45) that extends in the transverse direction and is tangent to the respective closure means on the crotch-facing side intersects the absorbent element (6).

8. The disposable incontinence diaper of claim 1, wherein each rearward side portion (22) has exactly one closure means (28).

9. The disposable incontinence diaper of claim 1, wherein the rearward side portions (22) are folded onto themselves about at least two side portion folding axes (46, 48) that run in the longitudinal direction (8), part-regions (50, 52, 54) of the rearward side portions (22) that are folded onto one another being defined and delimited by said side portion folding axes (46, 48), and in that a part-region (54) that is outboard in the transverse region (10) is configured so as to be substantially non-elongatable.

10. The disposable incontinence diaper of claim 9, wherein a part-region (52) that inwardly adjoins the outboard part-region (54), proceeding from the outer folding axis (48) that runs in the longitudinal direction, by way of at least 50% of the area of said part-region (52) is configured so as to be non-elongatable.

11. The disposable incontinence diaper of claim 9, wherein a respective side portion folding axis (46) that in the unfolded state is inboard, thus adjacent to the rearward lateral longitudinal periphery (18) of the main part (4), runs within the elastic or elasticized region (42) of the respective side portion (22).

12. The disposable incontinence diaper of claim 9 wherein a respective side portion folding axis (48) that in the unfolded state is further outboard in the transverse direction (10) runs within a non-elongatable region of the rearward side portions (22).

13. The disposable incontinence diaper of claim 9, wherein an extent (A) in the transverse direction (10) of the rearward side portions (22) that are folded onto themselves beyond the respective rearward lateral longitudinal periphery (18), and an extent (B) in the longitudinal direction (8) of the rearward side portions (22) that are folded onto themselves, are dimensioned such that the mutual ratio of the extents (NB) is 0.5<A/B<1.

14. The disposable incontinence diaper of claim 9, wherein the main part (4), together with the rearward side portions (22) that are folded inward onto themselves, is folded onto itself about a first and a second main part folding axis that in each case run in the longitudinal direction (8) in such a manner that the rearward side portions (22) on both sides come to lie so as to at least partially overlap one another in the direction of thickness.

15. The disposable incontinence diaper of claim 1, wherein the rearward side portions (22) are folded onto themselves about exactly two side portion folding axes (46, 48) that run in the longitudinal direction (8) such that exactly three part-regions (50, 52, 54) of the side portions (22) are formed, and in that the central part-region (52), proceeding from the outer folding axis (48) that runs in the longitudinal direction (8), by way of at least 50% of the area thereof is configured so as to be non-elongatable.

* * * * *